(12) United States Patent
Grolman

(10) Patent No.: US 6,361,495 B1
(45) Date of Patent: Mar. 26, 2002

(54) HAND-HELD NON-CONTACT TONOMETER

(75) Inventor: Bernard Grolman, Worcester, MA (US)

(73) Assignee: Leica Microsystems Inc., Depew, NY (US)

( * ) Notice: Subject to any disclaimer, the term of this patent is extended or adjusted under 35 U.S.C. 154(b) by 0 days.

(21) Appl. No.: 09/499,837

(22) Filed: Feb. 7, 2000

(51) Int. Cl.⁷ .................................................. A61B 3/16
(52) U.S. Cl. ...................................................... 600/401
(58) Field of Search ................................ 600/401, 405, 600/558; 351/208

(56) References Cited

U.S. PATENT DOCUMENTS

| | | |
|---|---|---|
| 3,181,351 A | 5/1965 | Stauffer |
| 3,232,099 A | 2/1966 | Motchenbacher |
| 3,538,754 A | 11/1970 | Grolman et al. |
| 3,585,849 A | 6/1971 | Grolman |
| 3,756,073 A | 9/1973 | Lavallee et al. |
| 3,832,890 A | 9/1974 | Grolman et al. |
| 4,192,317 A | 3/1980 | Munnerlyn et al. |
| 4,622,459 A | 11/1986 | Bouge et al. |
| 4,724,843 A | 2/1988 | Fisher |
| 4,747,296 A | 5/1988 | Feldon et al. |
| 4,817,620 A * | 4/1989 | Katsuragi et al. ........... 600/401 |
| 4,881,807 A | 11/1989 | Luce et al. |
| 4,951,670 A * | 8/1990 | Tanaka et al. ............... 600/401 |
| 5,101,826 A * | 4/1992 | Katsuragi ..................... 600/401 |
| 5,174,292 A | 12/1992 | Kursar |
| 5,299,573 A * | 4/1994 | Kobayashi .................... 600/401 |
| 6,159,148 A * | 12/2000 | Luce ........................... 600/405 |

* cited by examiner

Primary Examiner—Robert L. Nasser
Assistant Examiner—Brian Szmal
(74) Attorney, Agent, or Firm—Simpson, Simpson & Snyder, PLLC

(57) ABSTRACT

A hand-held non contact tonometer includes a piston having a transparent plane parallel window normal to a measurement axis of the tonometer along which the piston travels to discharge a fluid pulse without interfering with optical alignment functions of the instrument. In a first embodiment intended for home use by a patient, an alignment guidance system utilizing a concave mirror and a target source in a plane containing the center of curvature of the concave mirror present an alignment image to the patient for guiding self-alignment. An infra-red light source at the focal point of the concave mirror irradiates the concave mirror so that a collimated beam is reflected along the measurement axis and focused by an objective lens. When the focal point of the objective lens coincides with the center of curvature of the cornea, the infra-red light is retro-reflected through the system and diverted orthogonally from measurement axis to a masked detector to passively monitor alignment and trigger release of the piston. A second embodiment for office use by a general medical practitioner includes an eyepiece in place of the concave mirror for allowing operator observation along the measurement axis during alignment.

44 Claims, 6 Drawing Sheets

HAND-HELD NON-CONTACT TONOMETER

BACKGROUND OF THE INVENTION

A. Field of the Invention

The present invention relates to the field of ophthalmic instruments, and more particularly to hand-held non-contact tonometers intended for "at home" self-testing by patients and office use by general medical practitioners.

B. Description of the Prior Art

Ophthalmologists and optometrists use non-contact tonometers to screen patients for elevated intraocular pressure associated with glaucoma. In the therapeutic care of glaucoma patients, ophthalmologists are confronted with the nearly impossible objective of assuring intraocular pressure control during the long time intervals between patient visits. Around-the-clock intraocular pressure monitoring studies cast serious doubt upon the relevance of sporadic observations in assessment of intraocular pressure control. Many medical doctors have expressed the need for simple and inexpensive non-contact tonometric instrumentation that could be used by patients at home, especially patients who have exhibited nerve tissue loss. Also, it is recognized that a simple and inexpensive non-contact tonometer designed for office use by general medical practitioners could improve chances for early diagnosis.

Hand-held tonometers of the "contact" variety are well known, as exemplified by U.S. Pat. Nos. 4,192,317; 4,622,459; 4,747,296; and 5,174,292. For obvious reasons, these contact instruments are not suitable for self-measurement. Moreover, an operator's skill in testing can have a significant impact upon measurement results, thus rendering these instruments poorly suited for use by general medical practitioners. Patient discomfort is also a drawback of direct contact tonometers.

U.S. Pat. No. 4,724,843 describes a portable non-contact tonometer that includes a carrying case 102 for housing a pump used to generate a fluid pulse, and a detachable hand-held unit 100 connected to the pump by a flexible connection line 104 enclosing a fluid conduit. The described non-contact tonometer precludes self-measurement because an operator other than the patient is required for alignment of the hand-held unit relative to the eye. In addition, the instrument itself is complex and expensive to manufacture.

SUMMARY OF THE INVENTION

It is therefore an object of the present invention to provide a non-contact tonometer that is suitable for home use by a patient. Portability, hand-held alignment, guidance in self-alignment, low cost, and readily understandable measurement output are desirable characteristics of a first embodiment of the present invention for meeting the stated object.

It is another object of the present invention to provide a non-contact tonometer that is suitable for office or clinic use by general medical practitioners. Portability, hand-held alignment, low cost, and readily understandable measurement output are desirable characteristics of a second embodiment of the present invention for meeting the stated object.

It is a further object of the present invention to introduce improved compactness into the design of non-contact tonometers by using a piston that moves directly along a measurement axis of the tonometer.

It is yet a further object of the present invention to provide an alignment guidance system for an ophthalmic instrument such as a tonometer that enables a patient to align the instrument in three-dimensions relative to an eye to be tested for self-testing purposes.

The hand-held non-contact tonometer according to the first embodiment of the present invention generally comprises a measurement axis along which a fluid discharge tube extends for discharging a fluid pulse toward the eye. The fluid discharge tube communicates with a fluid plenum that is subject to rapid volume decrease and pressure increase by a piston biased for movement along the measurement axis from a loaded position to an unloaded position. The piston itself includes a transparent plane parallel window normal to the measurement axis for transmitting collimated target and passive alignment light.

A patient is guided in self-alignment of the measurement axis and distancing the fluid discharge tube relative to a corneal pole by an alignment guidance system presenting a visible alignment image to a patient. The alignment guidance system includes a concave mirror facing the eye, and a configured target source originating at the measurement axis and residing in a plane normal to the measurement axis containing the center of curvature of the concave mirror. Divergent light from the target source is reflected by the concave mirror to form an inverted and reverted image of the target source about the measurement axis when alignment is achieved, thus appearing to the patient as a predetermined configuration centered on the measurement axis.

A passive alignment system is preferably incorporated into the tonometer to generate a signal indicating that three-dimensional alignment has been achieved for activating an electro-mechanical trigger mechanism to release the piston. An infra-red light source positioned at a focal point of the concave mirror is masked on one side to emit divergent rays toward the concave mirror, which reflects the incident light as a collimated beam along the measurement axis toward the eye. Light is focused at the front focal point of an objective lens. When the focal point coincides with the center of curvature of the cornea upon proper alignment, light is corneally retro-reflected through the system and diverted by a beam splitter through a lens focusing the light at a pinhole detector. A pair of masks having annular cut-outs prevent light from reaching the pinhole detector unless criteria for three-dimensional alignment are met.

Corneal applanation is detected according to known reflectance principles using obliquely incident light and a detector on opposite sides of the measurement axis to provide an applanation signal. A pressure sensor is arranged to monitor pressure within the fluid plenum and provide a corresponding pressure signal. The applanation signal and pressure signal are then evaluated to determine intraocular pressure, and one of three color-coded light-emitting diodes is illuminated based on the range of intracular pressures—safe, borderline, or elevated—into which the measured intraocular pressure falls.

The hand-held non-contact tonometer according to the second embodiment of the present invention is generally similar to that of the first embodiment, however the alignment guidance system, including the concave mirror, is removed and a target source is positioned remotely from the measurement axis to enable an operator to view through an eyepiece located along the measurement axis opposite from the objective lens. A visible spectral component of the retro-reflected target source light passes through a dichroic mirror on the measurement axis for focusing by the eyepiece, while an infra-red spectral component of the light is diverted by the dichroic mirror to a masked detector for passively confirming alignment. A digital readout is preferred to directly report the measured intraocular pressure to the operating medical practitioner.

BRIEF DESCRIPTION OF THE DRAWINGS

The nature and mode of operation of the present invention will now be more fully described in the following detailed description of the preferred embodiments taken with the accompanying drawing figures, in which.

DETAILED DESCRIPTION OF THE PREFERRED EMBODIMENTS

Figure 1:
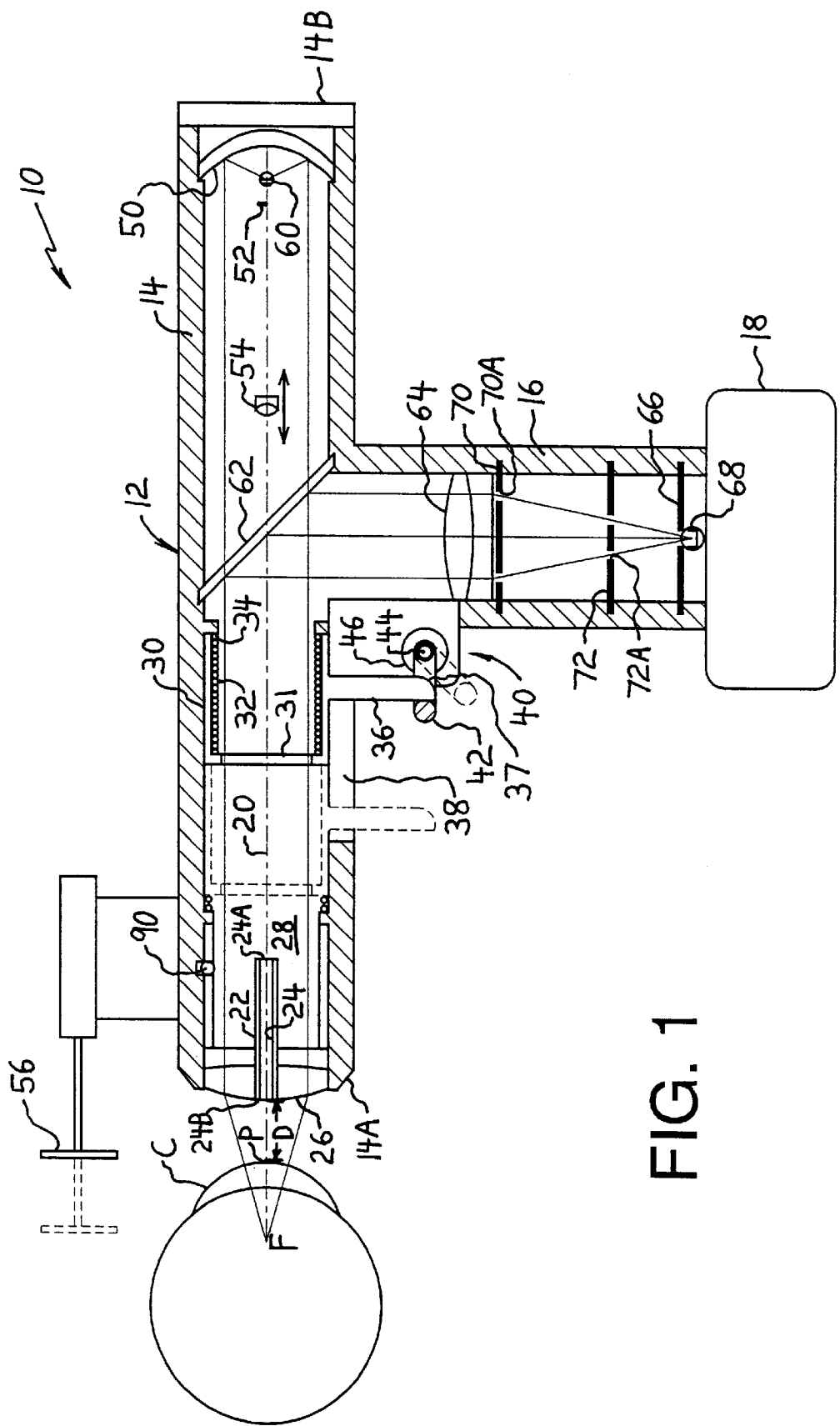
FIG. 1 is a schematic cross-sectional side view of a hand-held non-contact tonometer formed in accordance with a first embodiment of the present invention intended for patient home use.
Figure 2:
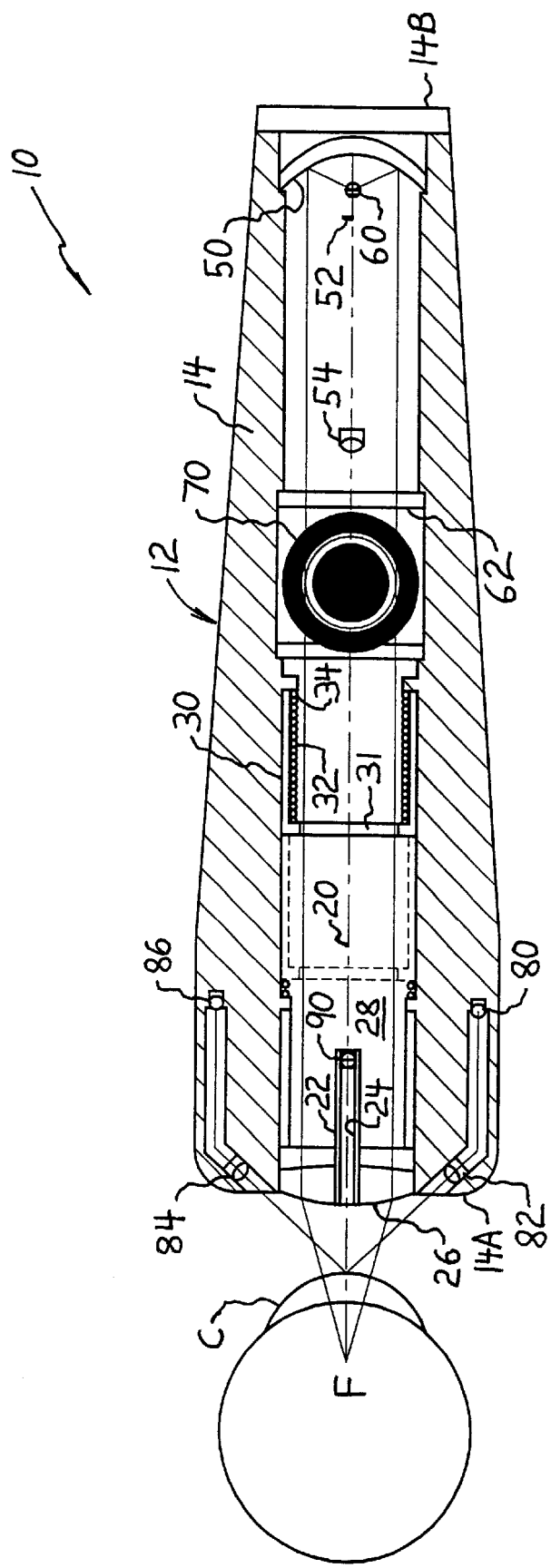
FIG. 2 is schematic top plan view of the hand-held non-contact tonometer shown in FIG. 1.

Reference is directed initially to FIGS. 1 and 2 of the drawings, wherein a hand-held non-contact tonometer formed in accordance with a first embodiment of the present invention is shown and designated generally by the reference numeral 10. Tonometer 10 is intended for home use by glaucoma patients for regularly monitoring intraocular pressure between visits to a supervising physician.

Tonometer 10 comprises a hollow housing 12 including a main tube 14 having a front end 14A and a rear end 14B, and a stem portion 16 joining with main tube 14 between front end 14A and rear end 14B. Housing 12 can be conveniently formed as a two-piece precision molding of mating halves designed with protrusions and recesses at various locations for mounting internal optical, mechanical and electrical components of tonometer 10. It will be appreciated that the configuration of housing 12 facilitates hand-held positioning of tonometer 10, since stem portion 16 provides a "handle" that a user can grasp. A battery pack 18 is situated at a bottom end of stem portion 16 for providing electric power to tonometer 10 without hindering portability, however AC power is a viable alternative or addition. It is contemplated to provide a wire frame stand (not shown) for stationary mounting of tonometer 10 on a table, if desired. Housing 12 is preferably adapted for mounting a flapper device (not shown) near front end 14A used to check instrument alignment and calibration in the field.

As with prior art non-contact tonometers, hand-held non-contact tonometer 10 of the present invention functions by directing a fluid pulse at cornea C to flatten or "applanate" a predetermined surface area of the cornea, monitoring a corresponding plenum pressure associated with the fluid pulse, and correlating the plenum pressure to intraocular pressure. Consequently, a measurement axis 20 along which the fluid pulse is directed is defined by a fluid discharge tube 22 having an axially extending fluid discharge passage 24 therethrough. Fluid discharge tube 22 is mounted at the front end 14A of housing main tube 14 by an objective lens 26 such that an entry end 24A of fluid discharge passage 24 resides in direct flow communication with a fluid plenum 28 provided in main tube 14. An exit end 24B of fluid discharge passage 24 is substantially flush with an outer surface of objective lens 26. Proper alignment of measurement axis 20 with corneal pole P, and proper location of exit end 24B at a predetermined firing distance D from corneal pole P, typically 11 mm, are necessary for measurement. Alignment of measurement axis 20 with corneal pole P can be thought of as alignment in the X and Y dimensions, while locating exit end 24B at a suitable firing distance D can be thought of as alignment in the Z dimension.

A piston 30 is mounted in main tube 14 for movement along measurement axis 20 between a loaded position, shown in solid line in FIGS. 1 and 2, and an unloaded position, shown in broken line in FIGS. 1 and 2. Piston 30 includes a transparent plane parallel window 31 normal to measurement axis 20 preferably formed of optical grade glass or optical grade plastic. Piston 30 is biased for movement from its loaded position to its unloaded position by a spring 32 bearing against an internal step 34 in main tube 14. A magnetic biasing means could also be employed. A trigger arm 36 connected to piston 30 extends through an elongated slot 38 in main tube 14 for enabling manual cocking or loading of piston 30 against the urging of spring 32. An electro-mechanical trigger mechanism 40 is housed adjacent an underside of main tube 14 and/or a front side of stem portion 16 for receiving and holding trigger arm 36 when piston 30 is in its loaded position. By way of non-limiting example, trigger mechanism is shown as including an L-shaped gate member 42 mounted for rotation about an axis defined by pivot pin 44 and biased by a torsion spring (not shown) to normally reside in the position shown in FIG. 2. A distal leg of gate member 42 blocks trigger arm 36 to hold piston 30 in its loaded position against the urging of spring 32. An automatic rotational drive means 46, such as a rotary solenoid or motor, is operably connected to drive gate member 42 in a counterclockwise angular direction to remove the distal leg of the gate member from blocking engagement with trigger arm 36 to release piston 30. Trigger arm 36 includes an arcuate surface 37 used during manual cocking or loading of piston 30 for urging gate member 42 to pivot slightly against its torsional bias to allow the trigger arm to move behind the gate member. The trigger mechanism described at present is meant to serve as an illustrative example of a possible electro-mechanical trigger mechanism, and it is acknowledged that many alternative electro-mechanical trigger mechanisms are conceivable by those of ordinary skill in the art. Such alternative trigger mechanisms are considered to be electro-mechanical trigger means under the claimed invention. It will be appreciated that the manually cocked piston also saves space and cost, however a fully automated return means for moving the piston to its loaded position can also be used without straying from the present invention.

Figure 4A:
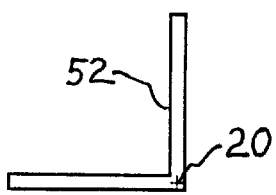
FIG. 4A is an enlarged view showing a self-luminous alignment target of the hand-held non-contact tonometer shown in FIGS. 1 and 2.
Figure 4B:
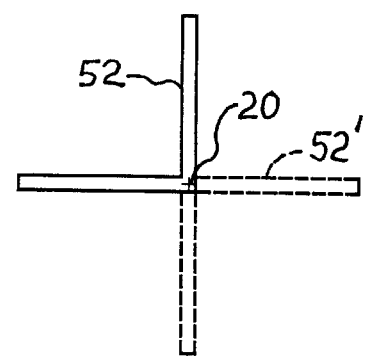
FIG. 4B is a representation of an alignment image as it would appear to a patient upon achieving proper alignment for the target configuration shown in FIG. 4A.
Figure 5A:
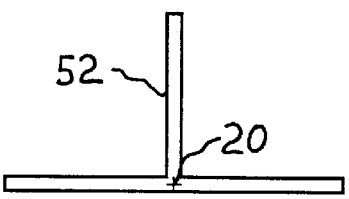
FIG. 5A is an enlarged view showing an alternative alignment target configuration for use in the hand-held non-contact tonometer shown in FIGS. 1 and 2.
Figure 5B:
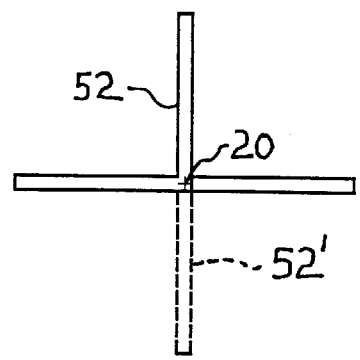
FIG. 5B is a representation of an alignment image as it would appear to a patient upon achieving proper alignment for the target configuration shown in FIG. 5A.
Figure 6A:
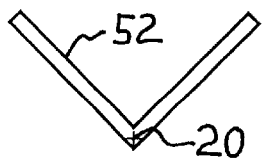
FIG. 6A is an enlarged view showing another alternative alignment target configuration for use in the hand-held non-contact tonometer shown in FIGS. 1 and 2.
Figure 6B:
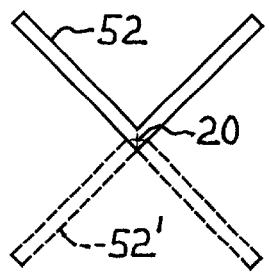
FIG. 6B is a representation of an alignment image as it would appear to a patient upon achieving proper alignment for the target configuration shown in FIG. 6A.

Tonometer 10 according to the first embodiment is provided with an alignment guidance system that produces an alignment image visible to the eye being measured to guide the patient/user in three-dimensional (X, Y, and Z) self-alignment relative to the eye. The alignment guidance system includes a concave mirror 50 centered on measurement axis 20 near rear end 14B of housing main tube 14 with its reflecting surface facing the eye, and a small self-luminous target 52 located in the plane containing the center of curvature of concave mirror 50. As shown in FIG. 4A, target 52 preferably comprises two orthogonal arms having a vertex coincident with measurement axis 20. Thus, the eye sees the target 52 itself, and an inverted and reverted image of the target formed by concave mirror 50. If there is XY alignment of corneal pole P with measurement axis 20, the alignment image appears as a completed cross to the patient, as shown for example in FIG. 4B. Reference numeral 52' in FIG. 4B indicates the portion of the viewed alignment image formed by concave mirror 50. If XY alignment is not achieved, the inverted and reverted portion 52' will appear displaced from the position shown in FIG. 4B and the alignment image will not appear as a cross. Of course, other configurations of target 52 are possible, including but not limited to an inverted T-shaped target (FIG. 5A) producing an alignment image appearing as a cross upon proper XY alignment (FIG. 5B), and a V-shaped target (FIG. 6A) producing an alignment image in the form of an X upon proper XY alignment (FIG. 6B). The focus condition of the alignment image as it appears to the user provides an indication of Z alignment status, with a focused alignment image indicating proper firing distance. To accommodate for different refractive vision characteristics among patients, a small compensating lens 54 is preferably mounted on measurement axis 20 between the eye and target 52. The axial position of compensating lens 54 can be adjusted for a particular patient by a supervising physician, as indicated by the double arrow in FIG. 1. Finally, a telescoping stabilizer 56 mounted atop main tube 14 engages the patient's forehead to facilitate Z dimension self-alignment.

While the patient is visually guided to align tonometer 10 by hand, a passive opto-electronic monitoring system determines when three-dimensional alignment criteria have been met and transmits a signal to trigger mechanism 40 to release trigger arm 36. For this purpose, a small light source 60 is located on measurement axis 20 at the focal point of concave mirror 50. Light source 60 emits light outside the visible spectrum, preferably infra-red light, and is masked on the side facing the eye so that only the full aperture of concave mirror 50 is irradiated. The infra-red light is reflected by concave mirror 50 as a collimated beam travelling along measurement axis 20 toward the eye. The collimated infra-red beam passes through a beam splitter 62 and piston window 31 before being focused at focal point F by objective lens 26. When focal point F coincides with the cornea's local center of curvature, all rays are retro-reflected back through objective lens 26 and piston window 31 to beam splitter 62. Upon reaching beam splitter 62, the retro-reflected infra-red light is reflected by the beam splitter in a direction orthogonal to measurement axis 20. The redirected infra-red light is focused by a focusing lens 64 through a pinhole occluder 66 to a light-sensitive detector 68. Interposed between focusing lens 64 and detector 68 are two masks 70 and 72 having respective annular cutouts 70A and 72A of decreasing diameter in the direction of travel toward detector 68. In a manner analogous to Scheiner disk focus techniques, the masks 70 and 72 preclude rays from reaching apertured detector 68 unless three-dimensional alignment criteria have been satisfied. Upon XYZ alignment, a voltage spike is generated by detector 68.

Figure 3:
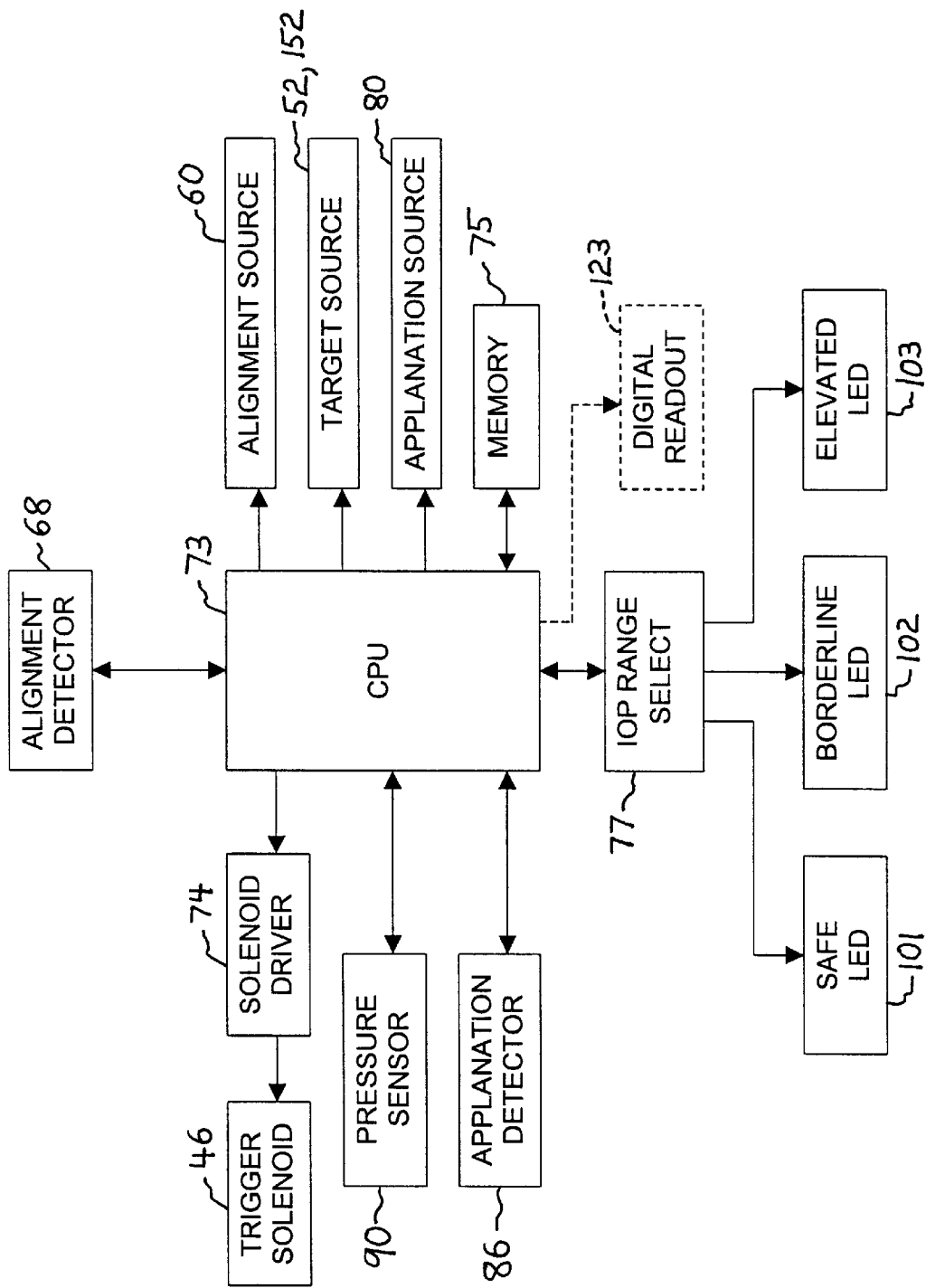
FIG. 3 is a schematic block diagram of electronic circuitry of the present invention.

Referring also now to the block diagram of FIG. 3, the signal from detector 68 is amplified and processed under the control of a central processing unit 73 to determine the existence of a voltage spike indicating three-dimensional alignment. When alignment is has been established, a signal is transmitted to solenoid driver 74 to energize rotational drive means 46 of trigger mechanism 40, thereby releasing piston 30 instantaneously. Piston 30 is forced along measurement axis 20 toward its unloaded position such that the volume of plenum 28 is rapidly decreased and the pressure within the plenum is rapidly increased, causing a fluid pulse to be discharged from the fluid discharge passage 24 of fluid discharge tube 22.

Tonometer 10 is equipped with applanation detection means, shown in FIG. 2, for monitoring corneal deformation caused by the fluid pulse and generating an applanation signal indicating the occurrence of corneal applanation. More specifically, an infra-red emitter 80 and collimating lens 82 direct an obliquely incident beam of light toward cornea C in the vicinity of corneal pole P, and a collector lens 84 and apertured detector 86 are positioned laterally and symmetrically opposite emitter 80 and collimating lens 82 relative to measurement axis 20. When cornea C is in its natural convex state, obliquely incident collimated light from emitter 80 is fanned out upon reflection by the curved surface of the cornea, thus resulting in a very low intensity signal at detector 86. The fluid pulse deforms cornea C from its original convex state, through an applanated state, to a concave state. When the corneal surface approximates a flat surface, the incident collimated light is reflected in a collimated manner from the corneal surface toward collector lens 84. Consequently, the intensity signal at detector 86 rises sharply during applanation and then falls off sharply as the cornea becomes concave. Consequently, a usually well-defined peak signal from detector 86 coincides with the moment of applanation. Other optical reflectance schemes are known in the tonometric art for determining applanation, with U.S. Pat. No. 3,538,754 by the present inventor being incorporated herein by reference for its teachings with regard to applanation detection. For sake of compactness, two fused bundles of very low numerical aperture optical fibers having distal ends angled to intersect at measurement axis 20 can be substituted for collimating lens 82 and collector lens 84.

A pressure sensor 90, for example a pressure transducer or the like, is placed within fluid plenum 28 to measure plenum pressure as the fluid pulse is generated. Pressure sensor 90 produces a signal proportional in magnitude to the fluid pressure in plenum 28.

The applanation and pressure signals are processed to find the plenum pressure at the moment of applanation. In this regard, tonometer 10 operates in a manner similar to non-contact tonometers of the prior art, such as the XPERT NCT available from Reichert Ophthalmic Instruments. A regression equation stored in memory 75 during clinical calibration of tonometer 10 allows the plenum pressure to be correlated to intraocular pressure measured in millimeters of mercury (mmHg). The intraocular pressure measurement result is reported to the patient in a manner that allows the result to be readily understood by the patient. The measurement result is preferably reported to the patient by illuminating one of three colored light-emitting diodes 101, 102, or 103 placed either externally on housing 12, as depicted in FIG. 2, or mounted internally for viewing through main tube 14. A green LED 101 is preferred for indicating an intraocular pressure within a "safe" safe range from, for example, 7 mmHg to 17 mmHg, an orange or yellow LED 102 is preferred for indicating an intraocular pressure within a "borderline" range as defined and set by the supervising physician depending on the specific needs and condition of the patient, and a red LED 103 is preferred for warning of an intraocular pressure within an "elevated"range above the borderline range. A range selection control 77 for setting the borderline intraocular pressure range is provided internally in tonometer 10 rather than externally to prevent patient adjustment thereof. Before tonometer 10 is issued to a patient, the supervising physician adjusts the borderline range and positions compensating lens 54 according to patient requirements.

Figure 7:
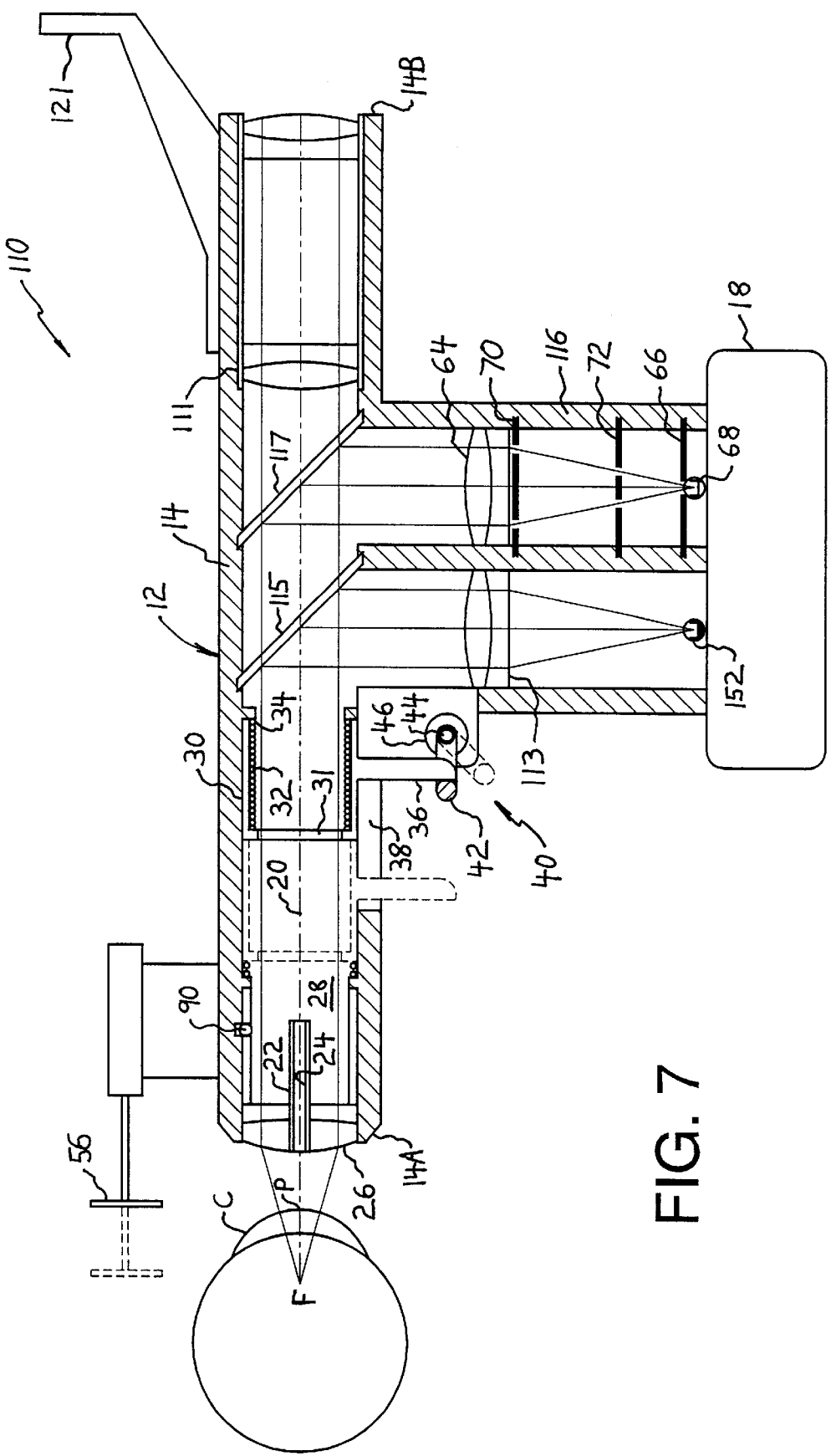
FIG. 7 is a schematic cross-sectional side view of a hand-held non-contact tonometer formed in accordance with a second embodiment of the present invention intended for office use by general medical practitioners.
Figure 8:
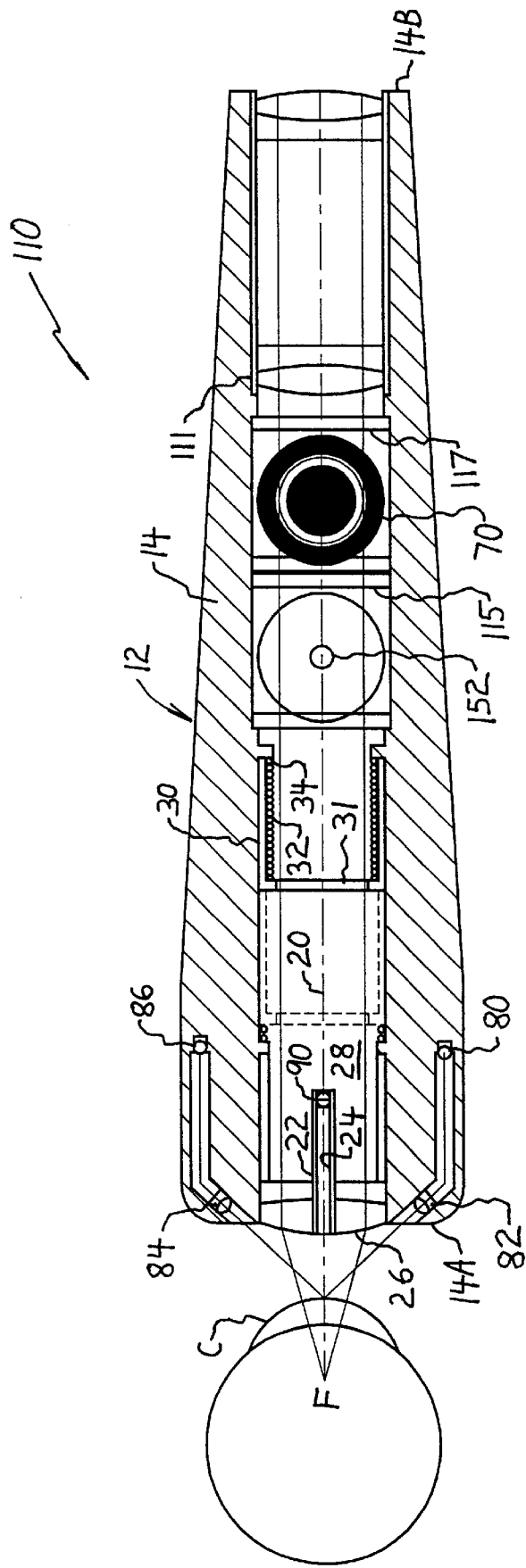
FIG. 8 is schematic top plan view of the hand-held non-contact tonometer shown in FIG. 7.

Attention is now directed to FIGS. 7 and 8 of the drawings showing a tonometer formed in accordance with a second embodiment of the present invention. Tonometer 110 is intended for office use by a general medical practitioner for early detection of elevated intraocular pressure. Tonometer 110 is similar to tonometer 10 of the first embodiment with respect to its measurement functions of fluid pulse generation, applanation detection, pressure sensing, and signal processing, with identical reference numbers indicating the same elements in each embodiment. Tonometer 110 differs from tonometer 10 of the first embodiment in that the self-alignment system used in the first embodiment is removed to allow an operator to visually perceive alignment directly along measurement axis 20 by looking through main tube 14 from rear end 14B toward the patient's eye.

In order to accommodate operator viewing, an adjustable focusing eyepiece 111 is provided at rear end 14B of main tube 14. A target source 152 emitting light in the visible and infra-red ranges is physically located in stem portion 116 off of measurement axis 20, and a lens 113 collimates light from target source 152 prior to forward reflection of the light by a beam splitter 115 positioned on measurement axis 20. The target light passes through piston window 31 and is focused at the front focal point F of objective lens 26. When focal point F is coincident with the center of curvature of cornea C, all incident rays are normal to the cornea and thus are retro-reflected by the cornea back through objective lens 26 for travel as a collimated beam along measurement axis 20. The corneally reflected light passes through piston window 31, beam splitter 115, and a dichroic mirror 117. Dichroic mirror 117 transmits visible spectral components of the light for focusing by eyepiece 111, thereby presenting a target image to an operator for assisting in alignment of tonometer 110. A fixed forehead rest 121 is preferably provided for the operator looking through eyepiece 111. Infra-red spectra are reflected by dichroic mirror 117 along a path orthogonal to measurement axis 20 to be used for passive alignment monitoring and trigger activation in the same manner described above in connection with the first embodiment. A digital readout 123, indicated in FIG. 3, is preferably substituted for the color-coded LED range reporting of the first embodiment to display a direct intraocular pressure value as measured by tonometer 110.

As will be appreciated from the above disclosure, the present invention provides inexpensive, portable, and self-usable tonometric instrumentation for patient home use and inexpensive, portable tonometric instrumentation for use by general physicians and the like. Tonometers 10 and 110 are manually alignable and automatically discharge a fluid pulse upon three-dimensional alignment to take a measurement.

What is claimed is:

1. A hand-held non-contact tonometer comprising:
   a measurement axis;
   a fluid discharge tube having a fluid discharge passage aligned on said measurement axis said fluid discharge passage having an entry end and an exit end;
   a fluid plenum in flow communication with said entry end of said fluid discharge passage;
   a piston movable between a loaded position and an unloaded position for increasing pressure within said plenum to discharge a fluid pulse from said exit end of said fluid discharge passage, said piston being movable along said measurement axis between said loaded and unloaded positions;
   alignment guidance means for presenting a visible alignment image to a patient for guiding said patient in self-alignment of said measurement axis with a corneal pole of an eye to be tested;
   applanation detection means for monitoring corneal deformation caused by said fluid pulse and generating an applanation signal indicating the occurrence of corneal applanation; a pressure sensor arranged to measure plenum pressure and generate a pressure signal corresponding to said plenum pressure;
   processing means for evaluating said applanation signal and said pressure signal to determine an intraocular pressure value; and
   reporting means for communicating a measurement result based on said intraocular pressure value.

2. The hand-held non-contact tonometer according to claim 1, wherein said piston includes a plane parallel window normal to said measurement axis.

3. The hand-held non-contact tonometer according to claim 1, further comprising biasing means for forcing said piston along said measurement axis from said loaded position to said unloaded position.

4. The hand-held non-contact tonometer according to claim 3, wherein said piston is manually movable along said measurement axis from said unloaded position to said loaded position against the urging of said biasing means.

5. The hand-held non-contact tonometer according to claim 3, wherein said biasing means is a spring.

6. A hand-held non-contact tonometer comprising:
   a measurement axis;
   a fluid discharge tube having a fluid discharge passage aligned on said measurement axis, said fluid discharge passage having an entry end and an exit end;
   a fluid plenum in flow communication with said entry end of said fluid discharge passage;
   a piston movable between a loaded position and an unloaded position for increasing pressure within said plenum to discharge a fluid pulse from said exit end of said fluid discharge passage;
   alignment guidance means for presenting a visible alignment image to a patient for guiding said patient in self-alignment of said measurement axis with a corneal pole of an eye to be tested, said alignment guidance means includes a concave mirror having a center of curvature on said measurement axis and a self-luminous target located in a plane containing said center of curvature normal to said measurement axis, whereby light from said target is reflected by said concave mirror to form an inverted and reverted image of said target about said measurement axis, and said guidance means guides said patient in self-alignment in three dimensions X, Y, and Z to align said measurement axis with said corneal pole and locate said exit end of said fluid discharge passage at a predetermined firing distance from said corneal pole;

applanation detection means for monitoring corneal deformation caused by said fluid pulse and generating an applanation signal indicating the occurrence of corneal applanation;

a pressure sensor arranged to measure plenum pressure and generate a pressure signal corresponding to said plenum pressure;

processing means for evaluating said applanation signal and said pressure signal to determine an intraocular pressure value; and reporting means for communicating a measurement result based on said intraocular pressure value.

7. The hand-held non-contact tonometer according to claim 6, wherein said target comprises a pair of orthogonal leg portions having a vertex on said measurement axis, whereby said alignment image appears as a cross upon X-Y alignment.

8. The hand-held non-contact tonometer according to claim 6, wherein said target comprises a pair of leg portions forming a V-shape having a vertex on said measurement axis, whereby said alignment image appears as an X-shape upon X-Y alignment.

9. The hand-held non-contact tonometer according to claim 6, wherein said target comprises a pair of orthogonal leg portions forming an inverted T-shape having an intersection on said measurement axis, whereby said alignment image appears as a cross upon X-Y alignment.

10. The hand-held non-contact tonometer according to claim 8, wherein Z alignment of said exit end of said fluid discharge passage is guided by the focus condition of said alignment image.

11. The hand-held non-contact tonometer according to claim 10, wherein said alignment guidance means further includes a correction lens adjustable along said measurement axis to compensate for patient refractive errors in viewing said alignment image.

12. The hand-held non-contact tonometer according to claim 1, further comprising an adjustable stabilizer for engaging the forehead of said patient.

13. The hand-held non-contact tonometer according to claim 3, further comprising electro-mechanical trigger means for holding said piston in said loaded position and releasing said piston to cause said fluid pulse to be discharged.

14. The hand-held non-contact tonometer according to claim 13, wherein said trigger means automatically releases said piston upon achievement of X-Y alignment of said measurement axis with said corneal pole and Z alignment of said exit end of said fluid discharge passage at a predetermined firing distance from said corneal pole.

15. The hand-held non-contact tonometer according to claim 14, wherein said electro-mechanical trigger means is operatively connected to an opto-clectronic alignment monitoring system, wherein said trigger means automatically releases said piston in response to an alignment signal generated by said alignment monitoring system at the instant X, Y, and Z alignment is achieved.

16. The hand-held non-contact tonometer according to claim 15, wherein said opto-electronic alignment monitoring system includes a non-visible light source on said measurement axis, a concave mirror facing said eye and having a focal point at said non-visible light source for receiving divergent light from said non-visible light source and reflecting a collimated beam of light toward said eye, an objective lens for focusing said collimated beam at an external focal point, a beam splitter on said measurement axis between said non-visible light source and said eye for receiving corneally reflected light and diverting said light from said measurement axis, a focusing lens for focusing said diverted light, a light-sensitive detector for receiving light from said focusing lens, and a pair of masks interposed between said focusing lens and said detector each having an annular cut-out for passing light focused on said detector by said focusing lens when XYZ alignment is achieved.

17. The hand-held non-contact tonometer according to claim 16, said concave mirror of said alignment guidance means and said concave mirror of said alignment monitoring system are the same mirror.

18. The hand-held non-contact tonometer according to claim 1, wherein said reporting means comprises a plurality of differently colored visible light sources each corresponding to a different predetermined range of intraocular pressures, and one of said plurality of visible light sources is illuminated based on the range of intraocular pressures into which said intraocular pressure value falls.

19. The hand-held non-contact tonometer according to claim 18, wherein said plurality of visible light sources comprises a first visible light source for indicating a safe range of intraocular pressures, a second visible light source for indicating a borderline range of intraocular pressures, and a third visible light source for indicating an unsafely elevated range of intraocular pressures.

20. The hand-held non-contact tonometer according to claim 19, wherein said first visible light source appears green.

21. The hand-held non-contact tonometer according to claim 19, wherein said second visible light source appears orange.

22. The hand-held non-contact tonometer according to claim 19, wherein said third visible light source appears red.

23. The hand-held non-contact tonometer according to claim 19, wherein said borderline range of intraocular pressures and said unsafely elevated range of intraocular pressures can be specifically adjusted for said patient.

24. A hand-held non-contact tonometer for measuring intraocular pressure in an eye, said non-contact tonometer comprising:

a measurement axis;

a fluid discharge tube having a fluid discharge passage aligned on said measurement axis, said fluid discharge passage having an entry end and an exit end;

a fluid plenum in flow communication with said entry end of said fluid discharge passage;

a piston movable along said measurement axis between a loaded position and an unloaded position for increasing pressure within said plenum to discharge a fluid pulse from said exit end of said fluid discharge passage, said piston including a plane parallel window normal to said measurement axis for transmitting light traveling parallel to said measurement axis without optical consequence irrespective of said piston's position along said measurement axis;

an opto-electronic alignment monitoring system for generating an alignment signal at the instant X, Y, and Z alignment is achieved;

applanation detection means for monitoring corneal deformation caused by said fluid pulse and generating an applanation signal indicating the occurrence of corneal applanation;

a pressure sensor arranged to measure plenum pressure and generate a pressure signal corresponding to said plenum pressure;

processing means for evaluating said applanation signal and said pressure signal to determine an intraocular pressure value; and reporting means for communicating a measurement result based on said intraocular pressure value.

25. The hand-held non-contact tonometer according to claim 24, further comprising an eyepiece aligned on said measurement axis, a target light source off of said measurement axis, a collimating lens after said target light source for receiving divergent light from said target source and forming a collimated beam of light, a beam splitter between said eyepiece and said eye for reflecting said collimated beam along said measurement axis toward said eye, an objective lens for focusing said collimated beam at an external focal point, and a dichroic mirror on said measurement axis for receiving corneally reflected light, said dichroic mirror transmitting visible light to said eyepiece and reflecting non-visible light for use by said alignment monitoring system.

26. The hand-held non-contact tonometer according to claim 25, wherein said beam splitter is between said piston and said eyepiece.

27. The hand-held non-contact tonometer according to claim 26, wherein said dichroic mirror is between said beam splitter and said eyepiece.

28. The hand-held non-contact tonometer according to claim 25, wherein said alignment monitoring system includes a focusing lens for focusing light received from said dichroic mirror, a light-sensitive detector for receiving light from said focusing lens, and a pair of masks interposed between said focusing lens and said detector each having an annular cut-out for passing light focused on said detector by said focusing lens when XYZ alignment is achieved.

29. The hand-held non-contact tonometer according to claim 24, further comprising biasing means for forcing said piston along said measurement axis from said loaded position to said unloaded position.

30. The hand-held non-contact tonometer according to claim 29, wherein said piston is manually movable along said measurement axis from said unloaded position to said loaded position against the urging of said biasing means.

31. The hand-held non-contact tonometer according to claim 29, wherein said biasing means is a spring.

32. The hand-held non-contact tonometer according to claim 24, further comprising an adjustable stabilizer for engaging the forehead of said patient.

33. The hand-held non-contact tonometer according to claim 24, further comprising a stabilizer for engaging the forehead of an operator.

34. The hand-held non-contact tonometer according to claim 29, further comprising electro-mechanical trigger means for holding said piston in said loaded position and releasing said piston to cause said fluid pulse to be discharged.

35. The hand-held non-contact tonometer according to claim 34, wherein said trigger means automatically releases said piston upon achievement of X-Y alignment of said measurement axis with said corneal pole and Z alignment of said exit end of said fluid discharge passage at a predetermined firing distance from said corneal pole.

36. The hand-held non-contact tonometer according to claim 35, wherein said electro-mechanical trigger means is operatively connected to said alignment monitoring system, wherein said trigger means automatically releases said piston in response to an alignment signal generated by said alignment monitoring system at the instant X, Y, and Z alignment is achieved.

37. The hand-held non-contact tonometer according to claim 24, wherein said reporting means comprises a digital readout for displaying said intraocular pressure value.

38. In a non-contact tonometer for measuring intraocular pressure of an eye by directing a fluid pulse along a measurement axis to deform the cornea of said eye, the improvement comprising a piston movable along said measurement axis to generate said fluid pulse, where in said piston includes a plane parallel window normal to said measurement axis for transmitting light traveling parallel to said measurement axis without optical consequence irrespective of said piston's position along said measurement axis.

39. An alignment guidance system for presenting a visible alignment image to a patient for guiding said patient in self-alignment of an ophthalmic instrument relative to an eye to be tested, said alignment guidance system comprising:

a self-luminous fixation target located on a measurement axis of said ophthalmic instrument; and a concave mirror having a center of curvature on said measurement axis, said target being located in a plane containing said center of curvature and being normal to said measurement axis;

whereby light from said target is reflected by said concave mirror to form an inverted and reverted image of said target about said measurement axis when said measurement axis is aligned with a direction of fixation of said eye.

40. The alignment guidance system according to claim 39, wherein said target comprises a pair of orthogonal leg portions having a vertex on said measurement axis, whereby said alignment image appears as a cross upon alignment of said measurement axis with said direction of fixation.

41. The alignment guidance system according to claim 39, wherein said target comprises a pair of leg portions forming a V-shape having a vertex on said measurement axis, whereby said alignment image appears as an X-shape upon X-Y alignment.

42. The alignment guidance system according to claim 39, wherein said target comprises a pair of orthogonal leg portions forming an inverted T-shape having an intersection on said measurement axis, whereby said alignment image appears as a cross upon X-Y alignment.

43. The alignment guidance system according to claim 39, wherein distance alignment of said ophthalmic instrument relative to said eye is guided by the focus condition of said alignment image.

44. The alignment guidance system according to claim 43, further comprising a correction lens adjustable along said measurement axis to compensate for patient refractive errors in viewing said alignment image.

* * * * *